United States Patent [19]

Harima

[11] Patent Number: 4,725,230

[45] Date of Patent: Feb. 16, 1988

[54] ORTHODONTIC WIRE RETAINER

[75] Inventor: Toshio Harima, Kobe, Japan

[73] Assignee: Yugen Kaisha K.O.L., Hyogo, Japan

[21] Appl. No.: 894,236

[22] Filed: Aug. 6, 1986

[51] Int. Cl.$^4$ .............................................. A61C 3/00
[52] U.S. Cl. ............................................ 433/18; 433/6
[58] Field of Search ................... 433/6, 18, 20, 21, 22, 433/24

[56] References Cited

U.S. PATENT DOCUMENTS

| | | | |
|---|---|---|---|
| 1,130,242 | 3/1915 | Bacon | 433/21 |
| 1,361,661 | 12/1920 | Alexander | 433/20 |
| 4,090,299 | 5/1978 | Williams | 433/18 |
| 4,413,978 | 11/1983 | Kurz | 433/6 |
| 4,472,138 | 9/1984 | Howe | 433/20 |

FOREIGN PATENT DOCUMENTS 595207  4/1934  Fed. Rep. of Germany ........ 433/18

Primary Examiner—John J. Wilson
Attorney, Agent, or Firm—Armstrong, Nikaido, Marmelstein & Kubovcik

[57] ABSTRACT

An orthodontic wire retainer for application to the dental arch following an orthodontic treatment, which includes a first metal wire laid along the posterior surface of a dental arch, a second metal wire laid along the anterior surface of the dental arch, and a third metal wire configured to fit between a canine and a premolar or between a premolar and a molar. The first and second metal wires are brazed to the third metal wire to provide an annular bridge resiliently supporting the dental arch. The third metal wire is configured to provide additional support with the second metal wire on the anterior surface of a tooth at one end of the dental arch and to retain an adjacent tooth external of the bridge.

6 Claims, 2 Drawing Figures

ORTHODONTIC WIRE RETAINER

BACKGROUND OF THE INVENTION

1. Field of the Invention

The present invention relates to an orthodontic wire retainer. More particularly, the present invention relates to an orthodontic wire retainer which is to be kept in place following an orthodontic treatment of the dental arch till fixation of the arch.

2. Description of the Prior Art

It is common practice to have an orthodontic retainer set in position for a fairly long time following an orthodontic treatment of the dental arch till fixation of the arch. If the dental arch following an orthodontic treatment is allowed to stand, it will return to the pre-treatment condition owing to the so-called "relapse" phenomenon. The retainer is mounted on the dental arch and kept in situ for some time to prevent occurrence of the above event. For this purpose, various types of retainers have heretofore been developed. As illustrated in FIG. 2, the typical conventional retainer is made in such a manner that a metal wire (1), for example a stainless steel wire or a cobalt-chromium wire, which is laid along the anterior surface of the dental arch, is made to extend to the posterior surface of the dental arch and this extension (2) is fixedly secured to a base (3) made of a synthetic resin such as a poly-epoxy compound and molded to fit into the palate.

Because of the presence of the base (3) made of a resin and having a comparatively large thickness in the palate, the conventional retainer not only causes a foreign body sensation in use but has the disadvantage that as the base interferes with the movement of the tongue, the user tends to have difficulties in conversation.

Furthermore, for the reason that said base (3) exists in the palate, the conventional retainer is difficult to use during eating and is often removed temporarily before meals. For the above reasons, it is near to impossibility to use the conventional retain continually so that the benefit of use of a retainer is greatly sacrificed.

In addition, orthodontic treatment is often accompanied by tooth extraction and in such cases the extraction space is at times expanded with time after the orthodontic treatment. Once such an extraction space is formed, the conventional orthodontic retainer cannot exhibit its orthodontic function fully, for its support for the dental arch is substantially solely provided by the metal wire (1) disposed along the anterior surface of the dental arch.

It is a principal object of the present invention to overcome the above-mentioned drawbacks of the conventional orthodontic retainer and provide an orthodontic wire retainer free of a resin base.

SUMMARY OF THE INVENTION

Developed for the foregoing purpose, the present invention is concerned with an orthodontic wire retainer for application to the dental arch following an orthodontic treatment, comprising a first metal wire (11) laid along the posterior surface of a dental arch, a second metal wire (12) laid along the anterior surface of the dental arch, and a third metal wire (13) fitting between a canine tooth (20) and a premolar (30) or between a premolar (30) and a molar (40), said first and second metal wires (11) and (12) being fused to said third metal wire (13) to constitute an annular bridge (14) providing a resilient support for the dental arch (10).

DETAILED DESCRIPTION OF THE INVENTION

Figure 1:
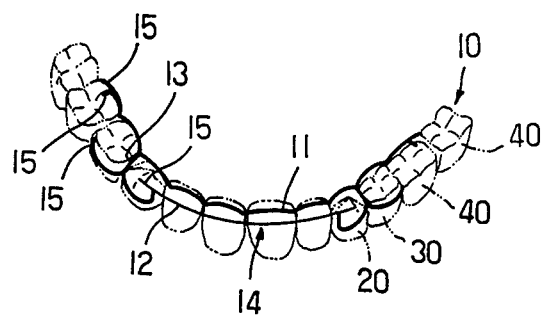
FIG. 1 is a front perspective view showing an orthodontic wire retainer according to the present invention.
Figure 2:
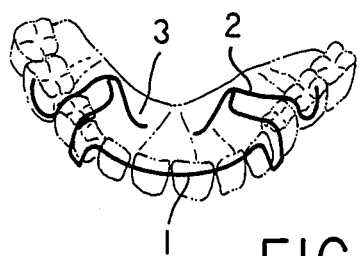
FIG. 2 is a front perspective view showing the conventional orthodontic retainer.

In accordance with the present invention, the first metal wire (11) disposed along the posterior surface of the dental arch (10), for example a fine gauge stainless steal wire or cobalt-chrominum wire, discharges the function of the synthetic resin base (3) of the conventional orthodontic retainer and, in cooperation with the second metal wire (12) disposed along the anterior surface of the dental arch, for example a stainless steel wire or cobalt-chromium wire which is finer in gauge than said first metal wire, and a third metal wire (13) that fits between a couple of teeth, for example a stainless steel wire or cobalt-chromium wire which is substantially identical in gauge with said first metal wire (11), constitutes an annular bridge (14) providing a resilient support for the dental arch.

DESCRIPTION OF THE PREFERRED EMBODIMENT

FIG. 1 is a front perspective view showing an orthodontic wire retainer according to the present invention. As illustrated, the orthodontic wire retainer comprises a stainless steel wire (11) about 1 mm in diameter extending along the posterior surface of the dental arch (10), a stainless steel wire (12) about 0.5 mm in diameter extending in a loop along the anterior surface of the dental arch (10), and a stainless steel wire (13) about 0.8 mm in diameter which fits between a canine tooth (20) and a premolar (30) and brazed in situ to said stainless steel wires (11) and (12). These stainless steel wires (11), (12) and (13) as brazed to each other constitutes an integral annular bridge (14) providing a resilient support for the dental arch to provide a dental arch bracing appliance that transmits the orthodontic pressure. In working the present invention, the diameters of stainless steel wires (11), (12) and (13) are selected according to the resilient bracing force to be applied to the dental arch. For example, the embodiment illustrated in FIG. 1 pertains to the case in which the relapsing force acting on the dental arch is directed toward the palate side and, therefore, in order to cope with this relapsing force, design consideration has been paid so that the first stainless steel wire (11) disposed along the posterior surface of the dental arch (10) has a diameter approximately twice that of the second stainless steel wire (12) disposed along the anterior surface of the dental arch (10).

In a preferred mode of working of the present invention, for the purpose of preventing sinking of the wire retainer with respect to the dental arch (10), the terminal ends of said first stainless steel wire (11), second stainless steel wire (12) and third stainless steel wire (13) are curved along the surfaces of the molar (40), premolar (30) and canine (20), respectively, to form rests (15). In this embodiment, the third stainless steel wire (13) is disposed between canine (20) and premolar (30) or between premolar (20) and molar (40) but in order to maintain the fitting and retention function of the wire retainer at a predetermined level, the position of said third stainless steel wire (13) is selected so that said rest (15) may exhibit the anti-sinking effect with respect to at least one premolar (30) or molar (40) externally of said annular bridge (14).

It will be apparent from the foregoing description that as the wire retainer according to the present invention is such that the metal wires transmit a resilient bracing force to the dental arch without the aid of a synthetic resin base, the difficulties in speech due to the placement of the resin base in the palate and the inconvenience of removing the retainer before meals are effectively eliminated. Therefore, the present invention permits long-term continued use of the retainer, thus bringing forth a marked improvement in orthodontic effect as compared with the conventional retainer.

I claim:

1. An orthodontic wire retainer for application to a dental arch following an orthodontic treatment, comprising a first metal wire adapted to conform with the posterior surface of a dental arch, a second metal wire adapted to conform with the anterior surface of the dental arch, and a third metal wire configured to fit between a canine and a premolar or between a premolar and a molar, said third metal wire being brazed to said first and second metal wires to constitute an annular bridge providing a resilient support for a plurality of teeth along the dental arch with one end of said third metal wire brazed to said second metal wire at a point spaced from one end of said second metal wire thereby providing a portion of said second metal wire extending beyond its brazed juncture with said third metal wire, said first metal wire supporting the posterior surface of at least one tooth at one end of said dental arch and said extended portion of said second metal wire and said third metal wire extending in spaced relation along a portion of the anterior surface of said one tooth whereby said one tooth is resiliently supported by said first metal wire on its posterior surface and by said second metal wire and said third metal wire on its anterior surface.

2. An orthodontic wire retainer according to claim 1 wherein the metal wires constituting said annular bridge are stainless steel wires.

3. An orthodontic wire retainer according to claim 1 wherein the metal wires constituting said annular bridge are cobalt-chromium wires.

4. An orthodontic wire retainer according to claim 1 wherein the diameter of said second metal wire is less than the diameter of said first and third metal wires and the relative diameters of said first, second and third metal wires constituting said annular bridge are such than an orthodontic pressure appropriate for prevention of a relapse is applied to the dental arch.

5. An orthodontic wire retainer according to claim 1 wherein said third metal wire is configured to extend along the anterior and posterior surfaces of a tooth adjacent to said one tooth at one end of said dental arch thereby retaining at least one tooth external of said annular bridge to said one tooth at one end of said dental arch.

6. An orthodontic wire retainer according to claim 5 wherein said one tooth at one end of said dental arch is a canine and the tooth adjacent to said one tooth is a premolar.

* * * * *